United States Patent
Pagnacco et al.

(10) Patent No.: US 7,163,516 B1
(45) Date of Patent: Jan. 16, 2007

(54) PATIENT DATA COLLECTION SYSTEM AND METHODS

(76) Inventors: Guido Pagnacco, 18002 Richmond Place Dr. #827, Tampa, FL (US) 33647; Elena Oggero, 18002 Richmond Place Dr. #827, Tampa, FL (US) 33647; A. Bob Henderson, 10240 Watreside Oaks Dr., Tampa, FL (US) 33647-3193

( * ) Notice: Subject to any disclaimer, the term of this patent is extended or adjusted under 35 U.S.C. 154(b) by 523 days.

(21) Appl. No.: 10/397,161

(22) Filed: Mar. 26, 2003

Related U.S. Application Data (63) Continuation-in-part of application No. 09/938,953, filed on Aug. 24, 2001, now abandoned.

(51) Int. Cl.
*A61B 5/00* (2006.01)
(52) U.S. Cl. ..................................... 600/595
(58) Field of Classification Search ................ 600/547, 600/587, 592; 33/512, 515
See application file for complete search history.

(56) References Cited

U.S. PATENT DOCUMENTS

| | | | | |
|---|---|---|---|---|
| 3,027,761 A | * | 4/1962 | Lauro ........................... | 73/172 |
| 3,596,725 A | | 8/1971 | Homs | |
| 3,724,574 A | * | 4/1973 | Hutchinson et al. .... | 177/210 R |
| 4,122,840 A | * | 10/1978 | Tsuchiya et al. ............ | 600/592 |
| 5,080,109 A | * | 1/1992 | Arme, Jr. ..................... | 600/595 |
| 5,415,176 A | * | 5/1995 | Sato et al. .................... | 600/547 |
| 5,590,648 A | * | 1/1997 | Mitchell et al. ............. | 600/301 |
| 5,694,199 A | | 12/1997 | Rodriguez | |
| 5,814,740 A | * | 9/1998 | Cook et al. ............. | 73/862.641 |
| 5,919,150 A | * | 7/1999 | Zanakis ....................... | 600/595 |
| 5,925,000 A | | 7/1999 | Marciniak et al. | |
| 6,038,465 A | * | 3/2000 | Melton, Jr. .................. | 600/407 |
| 6,256,532 B1 | | 7/2001 | Cha | |
| 6,258,032 B1 | * | 7/2001 | Hammesfahr ............... | 600/454 |
| 6,280,396 B1 | | 8/2001 | Clark | |
| D447,968 S | | 9/2001 | Pagnacco et al. | |
| 6,389,883 B1 | * | 5/2002 | Berme et al. ............... | 73/65.01 |
| 6,461,297 B1 | | 10/2002 | Pagnacco et al. | |
| 6,510,749 B1 | | 1/2003 | Pagnacco et al. | |
| 2001/0056249 A1 | * | 12/2001 | Savet ........................... | 600/587 |

FOREIGN PATENT DOCUMENTS

KR        2001037940 A        5/2001

* cited by examiner

*Primary Examiner*—Max Hindenburg
(74) *Attorney, Agent, or Firm*—Cahn & Samuels, LLP (57) ABSTRACT

A system for collecting patient screening data is disclosed. The system includes force measuring apparatus for measuring weight and for measuring balance forces, and stimuli delivery apparatus for delivering first stimuli designed to evaluate visual acuity, for delivering second stimuli designed to evaluate hearing acuity, and for accepting patient responses to the first stimuli and the second stimuli. A processing unit is associated with and manages the operation of the force measuring apparatus and the stimuli delivery apparatus for collecting weight and balance force measurements from the force measuring apparatus and patient responses from the stimuli delivery apparatus.

18 Claims, 7 Drawing Sheets

PATIENT DATA COLLECTION SYSTEM AND METHODS

CROSS-REFERENCE TO RELATED APPLICATIONS

This application is a continuation-in-part application from U.S. patent application Ser. No. 09/938,953, filed 24 Aug. 2001 now abandoned.

FIELD OF THE INVENTION

This invention relates to apparatus and methods identifying balance disorders, and to apparatus and methods for detecting and measuring biological functions in humans and for collecting patient screening data.

BACKGROUND OF THE INVENTION

Falls among patients, especially the elderly, is a rapidly growing problem, which costs patients and insurance companies over $20 billion each year. Fall prevention does not begin with knowing how to prevent falls. Rather, fall prevention lies in getting physicians, particularly primary care physicians, to identify and assess virtually every fall risk patient and every elderly patient. Making an assessment of a patient's fall risk requires a physical examination, an audiometric/otological evaluation, a focused patient medical history assessment, and a visual acuity test. Unfortunately, very few physicians incorporate fall risk assessment in their patient screening procedures, because to do so is time consuming, and requires specialized and expensive equipment including audiometric and otological testing equipment, and specialized training. Accordingly, most primary care physicians avoid making fall prevention assessments because it disrupts their work-flow, takes a great deal of their time, and requires specialized equipment and expertise.

Thus, what is needed are new and improved, cost-effective, and results-effective, apparatus and methods for identifying balance disorders in patients and for screening patients for balance disorders.

SUMMARY OF THE INVENTION

The above problems and others are at least partially solved and the above purposes and others realized in a system consisting of first apparatus for measuring weight and for measuring balance forces, and a second apparatus for delivering first stimuli designed to evaluate visual acuity, for delivering second stimuli designed to evaluate hearing acuity, and for accepting patient responses to the first stimuli and the second stimuli. A processing unit associated with the first apparatus and the second apparatus manages operation of the first apparatus and the second apparatus and is operative for collecting weight and balance force measurements from the first apparatus and patient responses from the second apparatus. An abutment is disposed away from and in opposition to the first apparatus, and measurement apparatus is provided for measuring the distance from the abutment to the first apparatus. By disposing the abutment on top of a patient's head while the patient is standing on the first apparatus, the patient's height can be ascertained. The system is configured with an input apparatus for accepting patient responses. The system is associated with storage, and the processing unit is adapted and arranged to store weight and balance force measurements from the first apparatus and patient responses from the second apparatus into the storage. Preferably, the processing unit is configured to conduct a screening process in approximately 60 seconds, in which the screening process includes a)an initiation by the processing unit of the first apparatus for collecting weight and balance force measurements, b)an initiation by the processing unit of the second apparatus for delivering first stimuli designed to evaluate visual acuity, delivering second stimuli designed to evaluate hearing acuity, and accepting patient responses to the first stimuli and the second stimuli, and c)a storing into the storage by the processing unit of collected weight and balance force measurements and collected patient responses to the first stimuli and the second stimuli.

Another embodiment of the invention is a system consisting of first apparatus for at least one of a)measuring weight, and b)measuring balance forces, and second apparatus for at least one of c)delivering first stimuli designed to evaluate visual acuity and accepting first patient responses thereto, and d)delivering second stimuli designed to evaluate hearing acuity and accepting second patient responses thereto. A processing unit is associated with the first apparatus and the second apparatus, which manages operation of the first apparatus and the second apparatus and collects at least one of weight measurements and balance force measurements from the first apparatus, and at least one of first patient responses and second patient responses. An abutment is disposed away from and in opposition to the first apparatus, and measurement apparatus is provided for measuring the distance from the abutment to the first apparatus. By disposing the abutment on top of a patient's head while the patient is standing on the first apparatus, the patient's height can be ascertained. The system is configured with an input apparatus for accepting at least one of first patient responses and second patient responses. The system is associated with storage, and the processing unit is adapted and arranged to store at least one of weight and balance force measurements from the first apparatus, and at least one of first patient responses and second patient responses from the second apparatus. Preferably, the processing unit is configured to conduct a screening process in approximately 60 seconds, in which the screening process includes a)an initiation by the processing unit of the first apparatus for collecting at least one of weight and balance force measurements, b)an initiation by the processing unit of the second apparatus for delivering at least one of first stimuli and second stimuli, c)an initiation by the processing unit of the second apparatus for accepting at least one of first patient responses and second patient responses, and d)a storing into the storage by the processing unit of at least one of collected weight and balance force measurements and at least one of collected first patient responses and second patient responses.

Yet another embodiment of the invention is a system consisting of apparatus for measuring weight and for measuring balance forces, and a processing unit associated with the apparatus for collecting weight measurements and balance force measurements from the apparatus. An abutment is disposed away from and in opposition to the apparatus, and measurement apparatus is provided for measuring the distance from the abutment to the apparatus. By disposing the abutment on top of a patient's head while the patient is standing on the apparatus, the patient's height can be ascertained. The system is associated with storage, and the processing unit is adapted and arranged to store weight and balance force measurements from the apparatus into the storage. Preferably, the processing unit is configured to conduct a screening process in approximately 60 seconds, in which the screening process includes a)an initiation by the processing unit of the apparatus for collecting weight and balance force measurements, and b)a storing into the storage by the processing unit of collected weight and balance force measurements from the apparatus.

Yet still another embodiment of the invention is a system consisting of apparatus for delivering first stimuli designed to evaluate visual acuity, for delivering second stimuli designed to evaluate hearing acuity, and for accepting patient responses to the first stimuli and the second stimuli, and a processing unit associated with the apparatus for managing operation of the apparatus and collecting patient responses from the apparatus. The system is associated with storage, and the processing unit is adapted and arranged to store patient responses from the apparatus into the storage. Preferably, the processing unit is configured to conduct a screening process in approximately 60 seconds, in which the screening process includes a)an initiation by the processing unit of the apparatus for delivering first stimuli designed to evaluate visual acuity, delivering second stimuli designed to evaluate hearing acuity, and accepting patient responses to the first stimuli and the second stimuli, and d)a storing into the storage by the processing unit of collected patient responses to the first stimuli and the second stimuli.

A further embodiment of the invention consists of a balance center model that incorporates a balance screening system including a force measuring apparatus for measuring weight and balance forces, which is linked to a computer and a printer. This balance screening system measures patient weight, calculates patient BMI and provides a patient stability/balance score, in which the patient name, age, sex and height are obtained and entered manually via the computer. Preferably, this process take place in approximately 60 seconds in accordance with the operation of the system as governed by a preprogrammed software architecture. With the use of the balance screening system in accordance with the instant embodiment, the balance center model of the invention functions to manage dizzy, balance disorder and falls risk patients, in which its underlying premise is that there are four steps to the effective management of such patients, namely, identification, assessment, diagnosis, and treatment.

Identification of a balance of falls risk patient is accomplished with the balance screening system, in accordance with the principle of the invention. The force measuring apparatus of the balance screening system identifies subjects with abnormal balance/sway/stability in through simple quiet standing, with eyes closed, on the force measuring apparatus. Perturbing foam can be placed on the force measuring apparatus for heightening balance/sway measurements. The computer of the balance screening system incorporates software having age-based normative data that can be compared to collected patient balance force data for identifying patients with balance problems and warn the doctor when the patient is at an increased risk of falling.

Assessment/testing of identified falls risk patients includes a focused history, a physical evaluation, audiometric testing and a visual acuity screening. A physician can obtain the focused history, physical evaluation and audiometric testing in the most cost and time effective way by referring the patient to ancillary medical personnel, as an audiologist and a physical therapist, or by delegating those tasks to someone within the physician's own staff, who can perform such tasks under the supervision of the physician, if needed. The visual acuity screening is a test of intermediate corrected vision of each eye independently, in which such test is to be carried out by the physician's staff when the patient returns to see the physician for a problem-focused visit to address the balance problem. In the usual case, the most cost and results effective diagnosis can be obtained from the patient's primary care physician when that physician has before him/her the results of focused history, audiometric evaluation, physical evaluation and visual acuity test. Patients who present with certain symptoms, or whose assessment/test results yield certain evidence or confusing results are be referred to the appropriate specialist. In terms of treatment, the overwhelming majority of patients will benefit from gait and balance therapy, and patients can either be referred to a physical therapist or such services can be performed by the physician or by someone under his/her supervision. Patients can also be referred to an occupational therapist for an assessment of the patient's medications, home environment, etc.

Consistent with the foregoing summary of the invention and the ensuing disclosure, the invention contemplates associated system and method embodiments.

BRIEF DESCRIPTION OF THE DRAWINGS

Referring to the drawings.

DETAILED DESCRIPTION OF A PREFERRED EMBODIMENT

There are now nearly 1,000 hip fractures each day in the United States, with 95% of them caused by falls. It is well understood that older people are not aware of their risks of falling, and neither recognize risk factors nor report these issues to their physicians. Because patients do not tell their physicians, their problem is never identified, so their physicians do not assess the patients for fall risk. Because physicians do not routinely make fall risk assessments, they do not intervene. As a result, balance problems often go undetected with risks becoming evident only after injury and disability have already occurred. To help overcome this problem, it is important and recommended that all physicians routinely assess patients, especially older patients, for risk of falling. Accordingly, the invention is concerned with providing physicians with a means to easily and efficiently assess patients for fall risk.

It is well understood that the best medical intervention strategy to employ to prevent falls is to first identify fall risk. It is therefore important to find and implement an effective and cost-efficient means to provide physicians with the ability to identify patient fall risk. Some physicians use a subjective approach, without any equipment, but this approach takes time and does not provide reliable and quantifiable results. The subsequent assessment of a balance patient takes even more time, because a focused medical history is the most important element of any assessment, and obtaining a history from older patients can be very time consuming. Another issue is the fact that physicians are unlikely to be fairly compensated for all the time they spend in properly assessing a balance patient.

Recognizing that physicians need a cost-effective, results-effective way to both quickly identify and to assess balance patients, the invention proposes in §I a new and improved PATIENT SCREENING APPARATUS and various embodiments and permutations thereof, and in §II new and improved APPARATUS AND METHODS FOR IDENTIFYING AND MANAGING BALANCE DISORDERS. A CONCLUSION in §III concludes the ensuing specification.

§A. Patient Screening Apparatus

Figure 1:
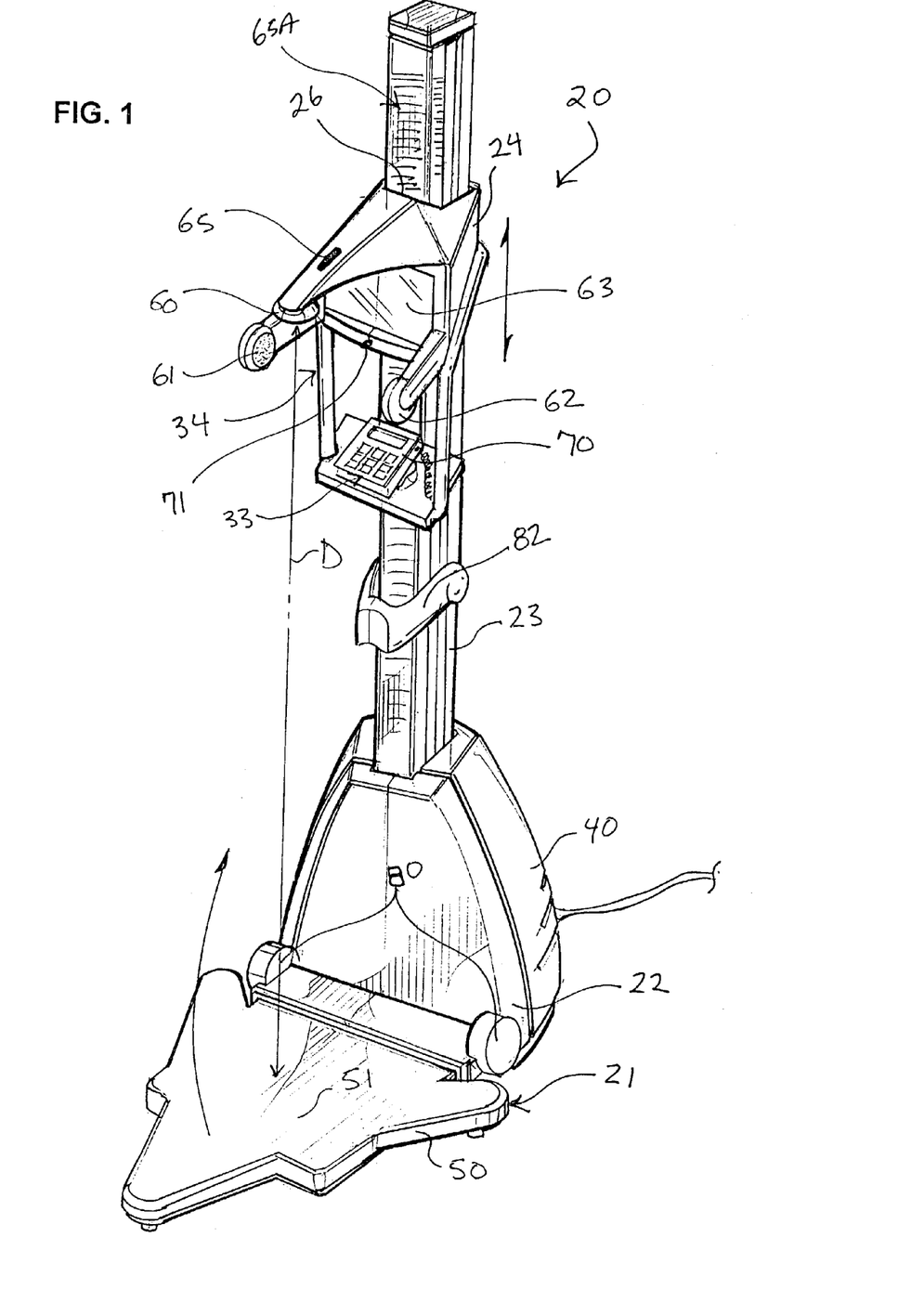
FIG. 1 is a perspective view of a system for collecting patient data, in accordance with the invention, including force measuring apparatus attached to a base, a carriage attached to a support projecting away from the base and having stimuli delivery apparatus and input apparatus for accepting patient responses to screening stimuli delivered by the stimuli delivery apparatus.

Turning now to the drawings, in which like reference characters indicate corresponding elements throughout the several views, attention is first directed to FIG. 1 in which is seen a system for collecting patient data, embodying the principle of the instant invention, generally indicated by the reference character 20 including force measuring apparatus 21 attached to a base 22 each positionable against the ground or other supporting surface. Looking also to FIGS. 2 and 3, an elongate support 23 is attached to and projects upwardly and away from base 22 and supports a carriage 24 away from apparatus 21. Carriage 24 is attached to a support 23 for reciprocal movement. In this embodiment, carriage 24 defines a socket 26 (shown only in FIG. 1) through which support 23 extends. Socket 26 captures support 23 and supports bearings, casters, sheaves or wheels that mate with and ride in grooves or channels formed along substantially the entire length of support 23 or a predetermined length thereof, which structure permits carriage 24 to move smoothly and reciprocally along support 23 and can be reversed. Carriage 24 can be reciprocally attached to support 23 in other ways, which will readily occur to the skilled artisan.

Figure 6:
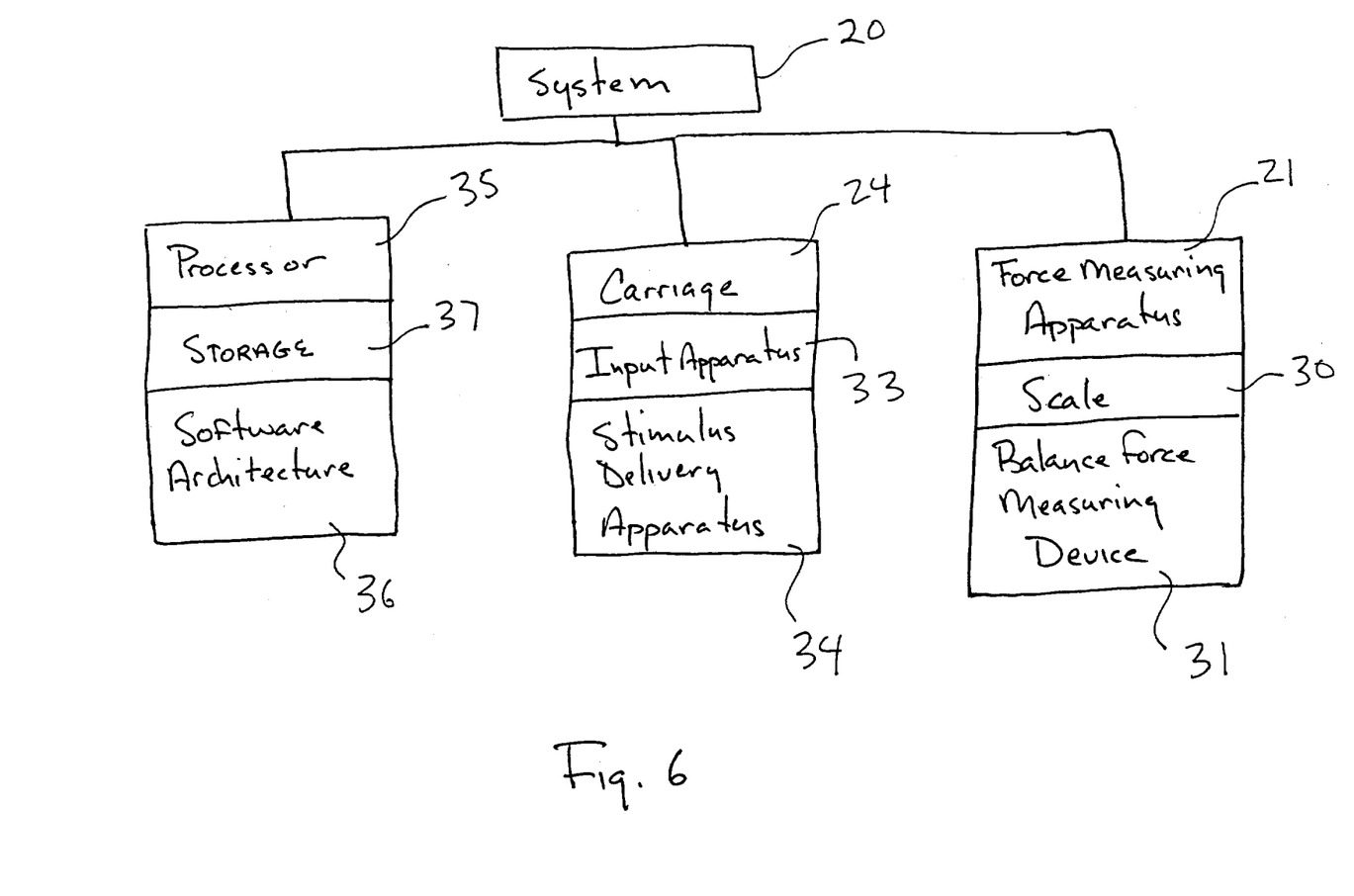
FIG. 6 is a schematic representation of the system of FIG. 1.

Looking momentarily to FIG. 6, which is a schematic representation of the various components of system 20, force measuring apparatus 21 measures weight and balance forces and thus includes a scale 30 component and a balance force measuring device 31 component. Carriage 24 supports input apparatus 33 and stimuli delivery apparatus 34, all of which are electronic components that communicate electronically with a computer or central processing unit 35. Processing unit 35 governs the operation of system 20 consistent with a preprogrammed software architecture 36, and is associated with electronic storage 37 for receiving and storing data and information from force measuring apparatus 21, stimuli delivery apparatus 34 and input apparatus 33 and this will be discussed in more detail infra. Input apparatus 33 can be considered part of stimuli delivery apparatus 34. It is to be understood that apparatus 21 and apparatus 34 can be operated and used independently of one another, in accordance with the teachings offered herein.

Figure 4:
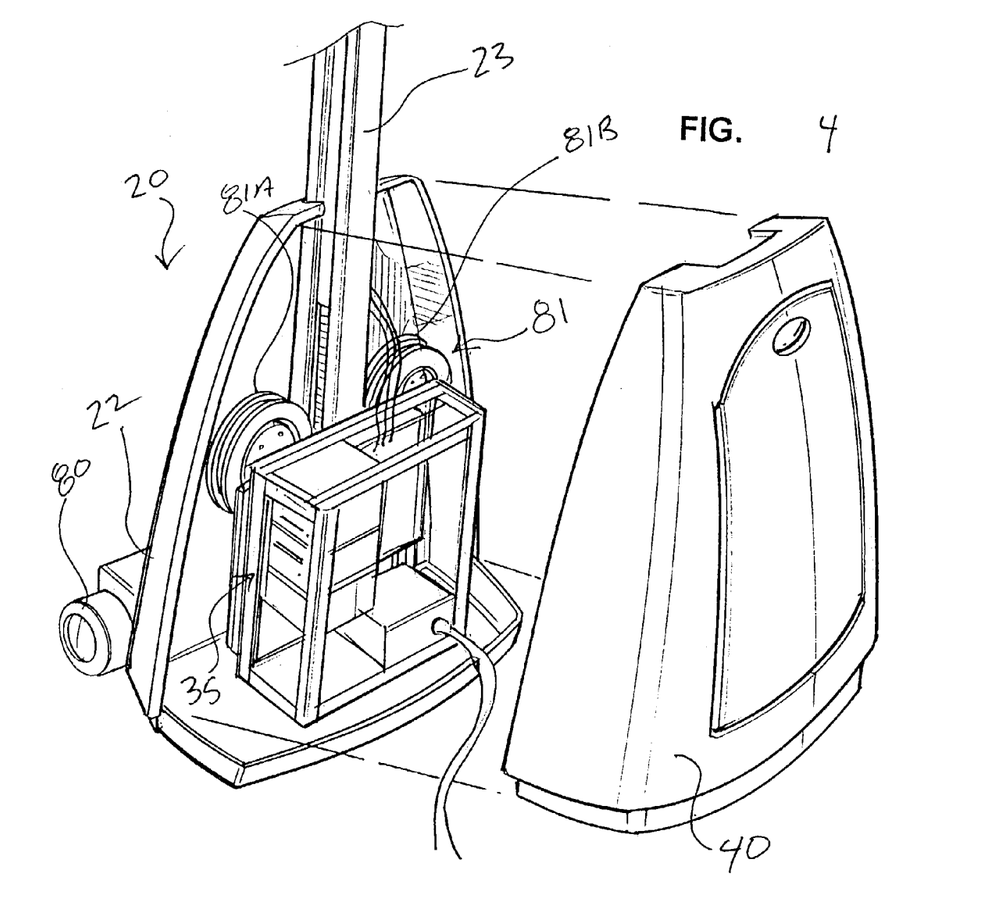
FIG. 4 is a fragmented perspective view of the system of FIG. 1 showing a cover of the base as it would appear detached therefrom.

Force measuring apparatus 21, input apparatus 33, stimuli delivery apparatus 34 and processing unit 35 are coupled together with conventional data transfer and electronic interconnections and wireless communication pathways can be used if desired. Preferably, processing unit 35 is housed within base 22 as shown in FIG. 4, although it can be housed elsewhere. Base 22 includes a housing that incorporates a removable cover 40 for facilitating access to processing unit 35 for maintenance, upgrading, etc. In the preferred embodiment disclosed, system 20 is self-contained and powered by a dedicated power source or a discrete power source, such as one or more rechargeable batteries.

Figure 2:
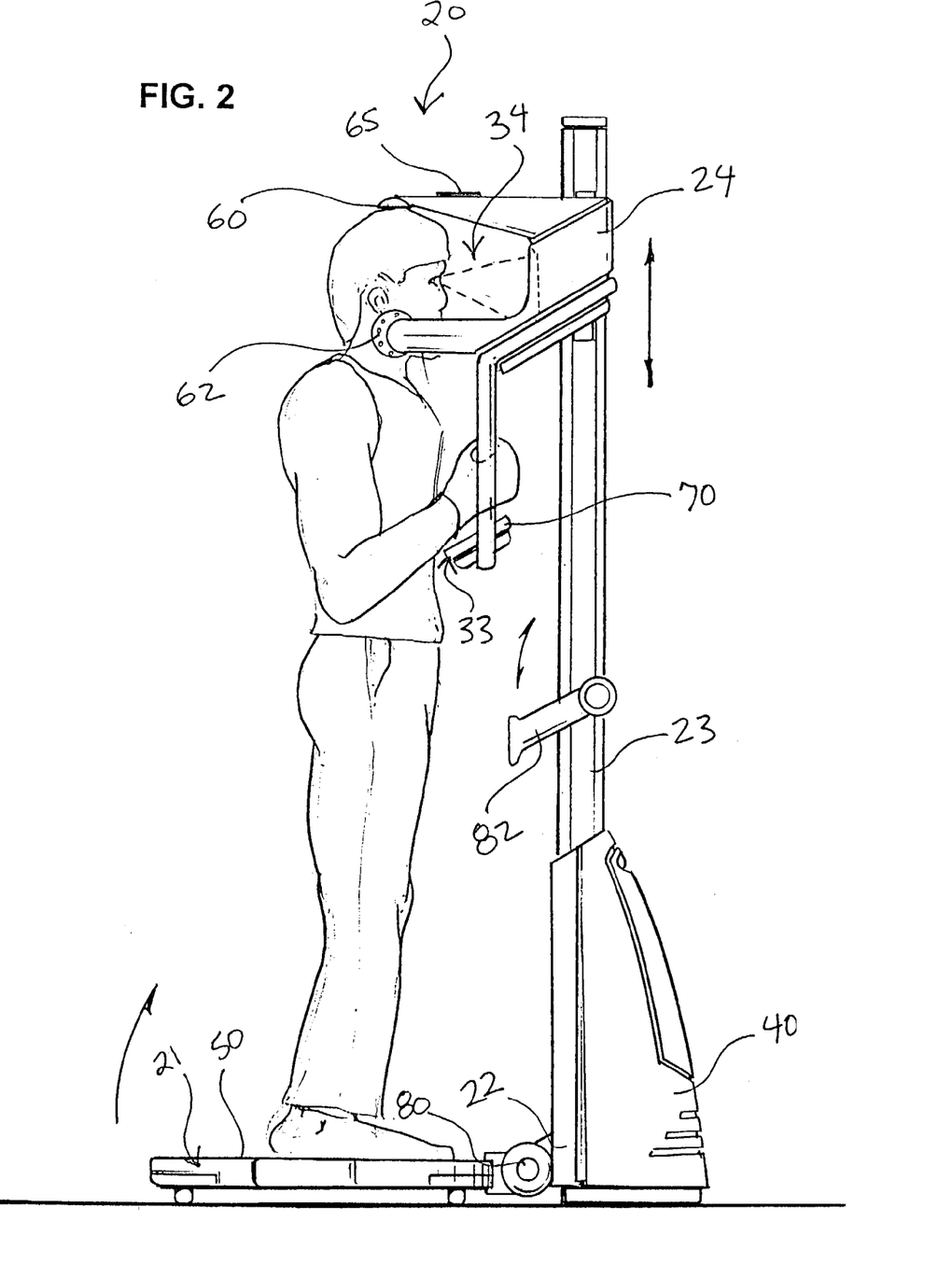
FIG. 2 is a side elevation of the system of FIG. 1 as it would appear in use.

Looking back to FIG. 1, force measuring apparatus 21 includes a housing 50 that supports and contains the scale 30 and balance force measuring device 31 components (scale 30 and device 31 components are referenced only in FIG. 6), and defines a load bearing surface 51 for accommodating a patient in a standing position as depicted in FIG. 2. The scale 30 and balance force measuring device 31 components of force measuring apparatus 21 are capable of measuring, respectively, the weight of and balance forces applied by a patient standing upon load bearing surface 51. In this regard, the scale 30 and balance force measuring device 31 components of apparatus 21 interact with load bearing surface 51 and are conventional and conventionally arranged in connection with one another and with load bearing surface 51. Scale 30 component is any conventional electronic scale arrangement for measuring weight and balance force measuring device 31 component is any conventional force platform arrangement for measuring force components and moments along one or more axes and along one or more associated orthogonal axes for use in measuring such forces exerted by a patient in varying forms of stance. It will be understood that apparatus 21 works under two modes of operation, namely, a weight measurement operation with scale 30 and a balance force measurement operation with force measuring device 31. Apparatus 21 can be configured to operate under these two modes simultaneously for taking weight measurements and balance force measurements at the same time, or at different times, namely, one mode after the other mode.

Figure 5:
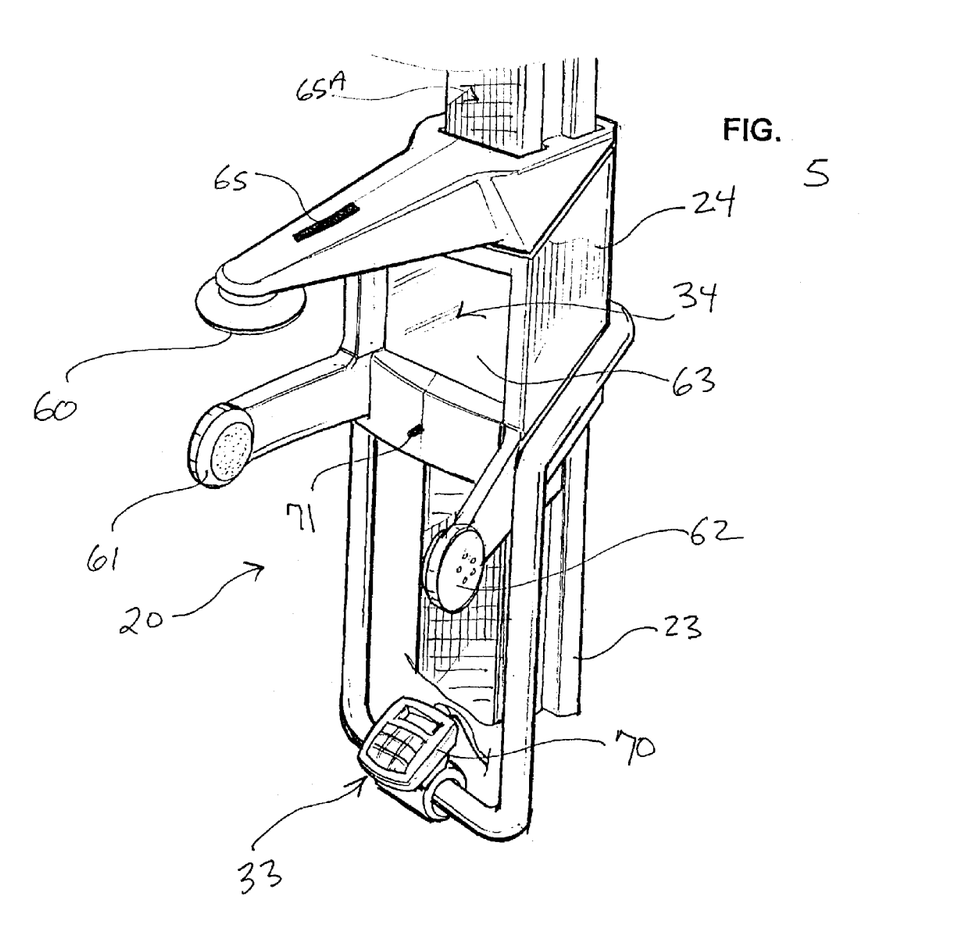
FIG. 5 is a fragmented perspective view of the system of FIG. 1 showing the carriage.

With continuing reference to FIG. 1 and further reference to FIG. 5, carriage 24 supports an abutment 60, speakers 61,62, a display 63 and input apparatus 33. Speakers 61,62 can be designed as headphones if desired. Speakers 61,62 and display 63 make up stimuli delivery apparatus 34, the operation of which is governed by processing unit 35. Processing unit 35 can be considered part of stimuli delivery apparatus 34 and, moreover, apparatus 21, if desired. Abutment 60 and speakers 61,62 extend away from support 23, overlie force measuring apparatus 21 and are situated in a triangular pattern adjacent display 63, which is located toward support 23, with abutment 60 located above and between speakers 61,62. As shown in FIGS. 1 and 2, abutment 60 is supported above and in direct opposition to load bearing surface 51 and is associated with a sensor 65 that is calibrated with a scale 65A supported along substantially the entire length of support 23 and that communicates with processing unit 35 and that, with its association with scale 65A, calculates the distance between abutment 60 and load bearing surface 51 at any position of carriage 24 along support 23. Scale 65A includes spaced-apart lines that are etched to or otherwise applied to a surface of support 32, which indicate distance from surface 51 of force measuring apparatus 21. Sensor 65 communicates or otherwise interacts with scale 65A, which are together with abutment 60 considered height measuring apparatus for measuring the distance between abutment 60 and apparatus 21, namely, surface 51 of apparatus 21. By disposing abutment 60 on top of a patient's head who is standing on surface 51 of apparatus 21, the patient's height can be ascertained with the height measuring apparatus.

Under direction of processing unit 35, speakers 61,62 issue audible acuity stimuli designed to ascertain/evaluate the hearing acuity of a patient, and display 63 issues visual acuity stimuli designed to ascertain/evaluate the visual acuity of a patient. In response to delivery of the audible acuity stimuli and the visual acuity stimuli, input apparatus 33 receives and accepts patient responses thereto, which responses are sent to and received by processing unit 35 and stored by processing unit 35 in storage 37. The audible acuity stimuli includes tones or other sounds that are issued in various frequencies and decibel levels, and the visual acuity stimuli includes visual displays, cues or charts and preferably the display of a Snellen chart or other similar chart for measuring visual acuity. Display 63 is a liquid crystal display or other desired display form. Display 63 can also be printed matter if desired.

In operation, a patient stands upon load bearing surface 51 of apparatus 21 as in FIG. 2 and directly beneath abutment 60 and carriage 24 is moved, either by the patient or by another, as necessary so as to present abutment 60 against the top of the patient's head. Carriage 24 is constructed in such a way such that speakers 61 and 62 reside at either side of a patient's head positioned therebetween with abutment 60 positioned against the top of the patient's head. While standing on load bearing surface 51 and with abutment 60 positioned against the top of the patient's head as shown, system 20 is actuated and a screening operation takes place in which the patient's weight, balance forces, height, visual acuity and hearing acuity are measured and recorded and stored. With regard to weight and balance forces, force measuring apparatus 21 measures the patient's weight and the balance forces exerted by the patient against load bearing surface 51, which weight and balance force measurements are sent to and received by processing unit 35 and stored in storage 37 as data. With abutment 60 positioned against the top of the patient's head and carriage 24 stationary, sensor 65 communicates with processing unit 35 and calculates the distance between abutment 60 and load bearing surface 51 which is the height of the patient, and communicates this height measurement to processing unit 35, which receives it and stores it in storage 37 as data.

In terms of screening the patient for audible acuity, the screening operation also includes audible acuity stimuli issued by speakers 61,62 in what is considered a hearing test event of the screening operation. In response to the issued audible acuity stimuli, the patient interacts with input apparatus 33 and submits responses to the delivery of the audible acuity stimuli, which responses are intended to be those that affirm his detection of any such tones or sounds or word utterances and the like. Processing system 35 governs the issuance of the audible acuity stimuli in accordance with preprogrammed parameters of software architecture 36, which issuance is responsive to responses input by the patient to the audible acuity stimuli. In the embodiment disclosed, input apparatus 33 is a keyboard or keypad 70 with which the patient can use and interact with for entering his responses. Keypad 70 is supported by an extension of carriage 24 at a location beneath display and toward support 23, and it can be supported elsewhere. Input apparatus 33 can also include a microphone 71 into which a patient can issue spoken responses. All patient responses are entered into and received by input apparatus 33 and communicated to and received by processing unit 35, which stores the responses into storage 37 as data.

In screening the patient for visual acuity, the screening operation also includes visual acuity stimuli issued by display 63 in what is considered a vision testing event. In response to the issued visual acuity stimuli, the patient interacts with input apparatus 33 and submits responses, which responses are intended to be those that affirm his ability to see such letters, visual cues, etc. Patient responses can be input at keypad 70 or into microphone 71 by means of verbal responses. All patient responses to the visual acuity stimuli are entered into and received by input apparatus 33 and communicated to and received by processing unit 35, which stores the responses into storage 37 as data.

The screening operation that system 20 provides, which is carried out when a patient is standing on load bearing surface 51 of force measuring apparatus 21 with abutment 60 positioned against the top of the patient's head, is thus characterized by the taking and storing of, in sequence and in any particular or desired order, the patient's height weight, balance forces, hearing acuity and visual acuity, with the taking and storing of the patient's hearing and visual acuity being patient responses to delivered hearing and visual acuity stimuli, which responses are stored in connection with the delivered stimuli. All of these data are stored into storage 37 by processing unit 35 in the form of an electronic document, which can be accessed and reviewed by clinical personnel and this can be done either with inputs received by keypad 70 or with a computer linked to system 20 and the latter is preferred. The screening operation can be carried out manually or automatically with preprogramming of processing unit 35. Actuation of system 20 for prosecuting a screening operation can occur in response to a patient standing on force measuring apparatus 21 and abutment 60 resting against the top of the patient's head or in response to a command input at keypad 70. The taking of the patient's height, weight, balance forces and hearing and visual acuity can take place in any desired order as previously intimated and even substantially simultaneously if desired.

Preferably, system 20 is a self-contained stand-alone unit having a relatively sleek and minimal design for taking up a small amount of space. Force measuring apparatus 21 is pivoted to base 22 at pivot joint 80 so that it can pivoted away from base 22 against a support surface as shown in FIGS. 1 and 2 for normal operation and toward and against base 22 for storage of system 20 when not in use. Although it is preferred that force measuring apparatus 21 be configured to measure weight and balance forces, it can be adapted for measuring only one or the other as may be desired. Keypad 70 is capable of accepting the input of specific patient information including patient's age, sex and details surrounding patient medical history and the input of this information can be delivered verbally and collected by microphone 71 if desired. After such patient information is input, it is delivered to processing unit 35 and stored in storage 37 as data.

Figure 3:
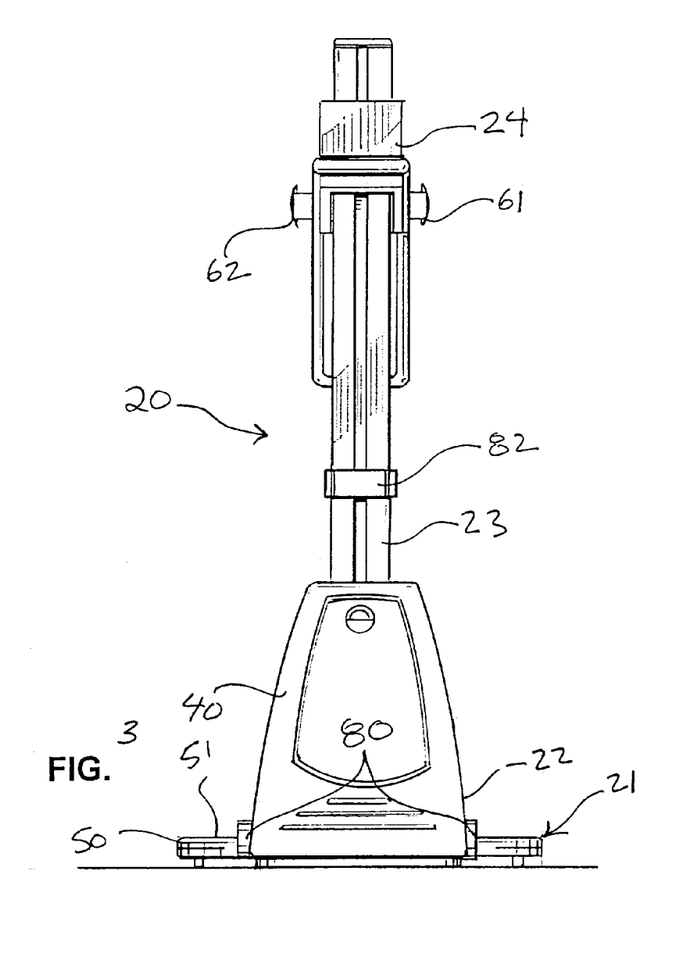
FIG. 3 is a rear elevation of the system of FIG. 1.

With momentary attention directed back to FIG. 4, a pulley system 81 is contained by base 22 and is coupled to carriage 24. Pulley system 81 includes positive and negative portions 81A,81B that permit carriage 24 to maintain position along support 23 yet be easily moved reciprocally from one location to another. FIGS. 1, 2 and 3 illustrate a locking lever 82 attached to support 23 that associates with force measuring apparatus 21. Lever 82 is capable of being pivoted/moved into a first position releasing force measuring apparatus 21 to permit it to be pivotally moved and a second position locking force measuring apparatus 21 in place both toward and against base 22 when system 20 is not in use and away from base as in FIGS. 1 and 2 when system 20 is in use and any conventional locking mechanism can be associated with lever 82 and force measuring apparatus 21 for carrying out this releasing and locking of force measuring apparatus 21.

And so the invention contemplates various embodiments of system 20 consisting of different combinations of elements thereof, which will now be summarized in no particular order are each considered separately from one another. In accordance with the teachings set forth herein, disclosed is system 20 that includes force measuring apparatus 21 for measuring weight and for measuring balance forces. Abutment 60 attached at a location spaced from and in opposition to apparatus 21. Apparatus 34 is provided for delivering screening stimuli proximate to abutment 60 and height measuring apparatus (namely, sensor 65 and scale 65A) is associated with abutment 60 for calculating height measurements between abutment 60 and apparatus 21. System 20 is furnished with input apparatus 33 for accepting patient responses to the screening stimuli, and processing unit 35 associated with apparatus 21 and apparatus 34 and the height measuring apparatus and input apparatus 33, and is configured to collect and store into storage 37 measured weight and balance forces from apparatus 21, patient responses from the input apparatus 33 (input apparatus 33 can be considered part of apparatus 34) and calculated height measurements between abutment 60 and apparatus 21 from the height measuring apparatus. System 20 is preferably self-contained and well constructed and relatively small and easy to move, and apparatus 21 is pivoted to base 22 of system 20 so that it can be moved between deployed and stored conditions. System 20 is furnished with carriage 24, which is reciprocated to support 23 projecting away from base 22, which supports abutment 60 and incorporates apparatus 34. The screening stimuli are visual acuity stimuli designed to evaluate visual acuity, and apparatus 34 includes display 63 that displays the visual acuity stimuli. Sensor 65 of the height measuring communicates with processing unit 35 and sends height measurements to processing unit 35 for storage. The screening stimuli are also audible acuity stimuli designed to evaluate hearing acuity, in which apparatus 34 incorporates speakers 61,62 that issue the audible acuity stimuli. Input apparatus 33 can be configured with microphone 71 for accepting verbal patient responses to the issued stimuli and/or keypad 70 for accepting input patient responses to the issued stimuli and preferably both are provided for convenience. Keypad 70 also accepts the input of specific patient information including patient age, sex and details surrounding patient medical history and the input of this information can be delivered verbally and collected by microphone 71 if desired.

Another embodiment of system 20 includes apparatus 21 for measuring weight and for measuring balance forces, and apparatus 34 for delivering first stimuli designed to evaluate visual acuity, for delivering second stimuli designed to evaluate hearing acuity, and for accepting patient responses to the first stimuli and the second stimuli. Processing unit 35 is associated with and manages the operation of apparatus 21 and apparatus 34, and is operative for collecting weight and balance force measurements from apparatus 21 and patient responses from apparatus 34. Abutment 60 is disposed away from and in opposition to apparatus 21, and height measurement apparatus (namely, sensor 65 and scale 65A as disclosed) is provided and associated with abutment 60, and is operative for measuring the distance from abutment 60 to apparatus 21 and communicating height measurements to processing unit 35. By disposing abutment 60 on top of a patient's head while the patient is standing on apparatus 21, the patient's height can be ascertained with the height measurement apparatus. System 20 is configured with input apparatus 33 for accepting the patient responses. System 20 is associated with storage 37, and processing unit 35 is adapted and arranged to store weight and balance force measurements from apparatus 21 and patient responses from apparatus 34 into storage 37. In this embodiment, processing unit 35 is configured by programming offered by software architecture 36 to conduct a screening process in approximately 60 seconds, in which the screening process includes a) an initiation/actuation for a predetermined period of time by processing unit 35 of apparatus 21 for collecting weight and balance force measurements, b) an initiation/actuation for a predetermined period of time by processing unit 35 of apparatus 34 for delivering first stimuli designed to evaluate visual acuity, delivering second stimuli designed to evaluate hearing acuity, and accepting patient responses to the first stimuli and the second stimuli, and c) a storing into storage 37 by processing unit 35 of collected weight and balance force measurements and collected patient responses to the first stimuli and the second stimuli.

Yet another embodiment of system 20 includes apparatus 21 configured for at least one of a) measuring weight, and b) measuring balance forces, and apparatus 34 configured for at least one of c) delivering first stimuli designed to evaluate visual acuity and accepting first patient responses thereto, and d) delivering second stimuli designed to evaluate hearing acuity and accepting second patient responses thereto. Processing unit 35 is associated with and manages the operation of apparatus 21 and apparatus 34 and collects at least one of weight measurements and balance force measurements from apparatus 21, and at least one of first patient responses and second patient responses from apparatus 34. Abutment 60 is disposed away from and in opposition to apparatus 21, and height measurement apparatus (namely, sensor 65 and scale 65A as disclosed) is provided for measuring the distance from abutment 60 to apparatus 21. By disposing abutment 60 on top of a patient's head while the patient is standing on apparatus 21, the patient's height can be ascertained. System 20 is configured with input apparatus 33 for accepting at least one of first patient responses and second patient responses. System 20 is associated with storage 37, and processing unit 35 is adapted and arranged to store at least one of weight and balance force measurements from apparatus 21, and at least one of first patient responses and second patient responses from apparatus 34. In this embodiment, processing unit 35 is configured by programming offered by software architecture 36 to conduct a screening process in approximately 60 seconds, in which the screening process includes a) an initiation/actuation for a predetermined period of time by processing unit 35 of apparatus 21 for collecting at least one of weight and balance force measurements, b) an initiation/actuation for a predetermined period of time by processing unit 35 of apparatus 34 for delivering at least one of first stimuli and second stimuli, c) an initiation/actuation for a predetermined period of time by processing unit 35 of apparatus 34 for accepting at least one of first patient responses and second patient responses, and d) a storing into storage 37 by processing unit 35 of at least one of collected weight and balance force measurements and at least one of collected first patient responses and second patient responses.

Yet still another embodiment of system 20 includes apparatus 21 for measuring weight and for measuring balance forces, and processing unit 35 associated with apparatus 21 for collecting weight measurements and balance force measurements from apparatus 21. Abutment 60 is disposed away from and in opposition to apparatus 21, and height measurement apparatus (namely, sensor 65 and scale 65A as described) is provided for measuring the distance from abutment 65 to apparatus 21. By disposing abutment 60 on top of a patient's head while the patient is standing on apparatus 21, the patient's height can be ascertained. System 20 is associated with storage 37, and processing unit 35 is adapted and arranged to store weight and balance force measurements from apparatus 21 into storage 37. In this embodiment, processing unit 35 is configured by programming offered by software architecture 36 to conduct a screening process in approximately 60 seconds, in which the screening process includes a)an initiation/actuation by processing unit 35 of apparatus 21 for collecting weight and balance force measurements, and b)a storing into the storage by processing unit 35 of collected weight and balance force measurements from apparatus 21.

A further embodiment of system 20 includes apparatus 34 for delivering first stimuli designed to evaluate visual acuity, for delivering second stimuli designed to evaluate hearing acuity, and for accepting patient responses to the first stimuli and the second stimuli, and processing unit 35 associated with apparatus 34 for managing operation of apparatus 34 and collecting patient responses from apparatus 34. System 20 is associated with storage 37, and processing unit 35 is adapted and arranged to store patient responses from apparatus 34 into the storage. In this embodiment, processing unit 35 is configured by programming offered by software architecture 36 to conduct a screening process in approximately 60 seconds, in which the screening process includes a)an initiation/actuation by processing unit 35 of apparatus 34 for delivering first stimuli designed to evaluate visual acuity, delivering second stimuli designed to evaluate hearing acuity, and accepting patient responses to the first stimuli and the second stimuli, and b)a storing into the storage by processing unit 35 of collected patient responses to the first stimuli and the second stimuli.

§B. Apparatus and Methods for Identifying and Managing Balance Disorders

The invention proposes implementing a multi-disciplinary "virtual balance center" by teaming together a primary care physician, audiologist and physical therapist, that incorporates early identification, assessment and treatment of balance patients. Looking to FIG. 7, the underpinning of this balance center model or system is a balance screening/assessment system 90, which consists of force measuring apparatus 100 that is linked to a computer 101 and a printer 102, in which the operation of force measuring apparatus 100 is managed by computer 101 in accordance with a pre-programmed software architecture 103. Preferably, force measuring apparatus 100 is of the type disclosed in U.S. Pat. No. 6,510,749 entitled FORCE MEASURING APPARATUS, which is incorporated herein by reference. It is to be understood, however, that any conventional force platform arrangement for measuring force components and moments along one or more axes and along one or more associated orthogonal axes for use in measuring such forces exerted by a patient in varying forms of stance can be used for force measuring apparatus 100.

Figure 7:
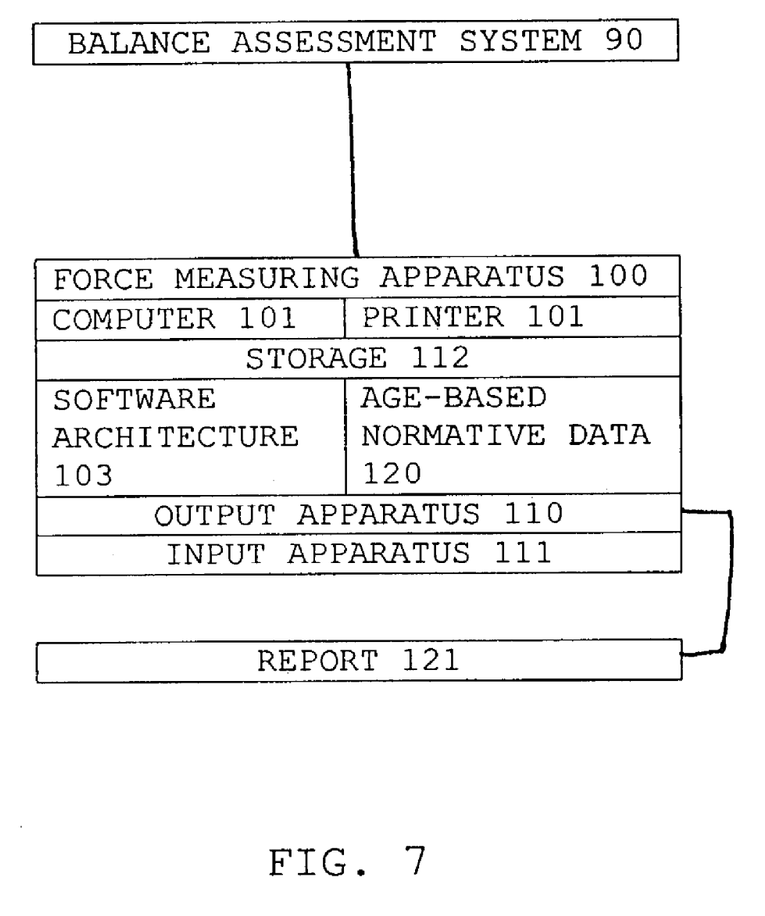
FIG. 7 is a schematic representation of a balance screening system.

Computer 100 is a personal computer, which is associated with output apparatus 110, such as a monitor or display, and input apparatus 111 such as a keyboard, a pointing device, voice command architecture incorporating a microphone and voice command recognition software, etc. Computer 20 is furnished or otherwise associated with storage 112, which houses and maintains, among other things, software architecture 103 and an operating system or platform and preferably one that is multi-tasking and responsive to inputs for accessing data and controlling the operation of force measuring apparatus 100 by way of software architecture 103. Input apparatus 111 is capable of accepting the input of specific patient information including patient's age, sex, height, body weight, etc. After such patient information is input, it is delivered to processing unit 35 and stored in storage 37 as data. In accordance with a preferred embodiment, software architecture 103 is furnished with a body-mass index (BMI) calculator, which calculates BMI from input of a user's height and weight, whether input in metric values or American values.

System 90 is useful for screening a patient and obtaining a printed report with the patient's age, sex, height, weight, BMI and stability/balance score. In typical screening procedure/operation, a patient's age, sex, height and weight are entered into computer 101 with input apparatus 111, in which computer 101 calculates the patient's BMI with the patient's entered height and weight values. Like force measuring apparatus 21 discussed supra, force measuring apparatus 100 can be configured to not only measure balance forces but also weight. In this regard, rather than entering weight into computer 101 via input apparatus 111, weight can be taken and measured by force measuring apparatus 100. The patient is directed to stand on force measuring apparatus 100, and system 90 is initiated/actuated and a balance screening takes place. System 90 is made to actuate to carry out a balance screening either manually in response to commands entered into computer 101 via input apparatus 111 or automatically by computer 101 in response to a patient standing on force measuring apparatus 100. Storage 112 maintains age-based normative data 120, which define normal age-based balance/stability parameters. Computer 101 accesses the specific age-based balance/stability parameters based on the patient's input age. Simply by directing the patient to stand quietly on force measuring apparatus 100 with his eyes closed for a predetermined period of time, force measuring apparatus 100 collects the balance/sway/stability forces exerted thereagainst by the patient and stored into storage 112 as patient force data. After the balance screening is complete, computer 101, either in response to commands entered via input apparatus 111 or automatically in accordance with programming provided for by software architecture 103, compares the patient force data to the appropriate age-based balance/stability parameters of normative data 120 and calculates a stability/balance score for the patient, and generates a report 121, which is printed by printer 102 and, optionally, stored into storage 112 as an electronic document. Report 121 sets forth patient's age, sex, height, weight, BMI and stability/balance score. Preferably, this screening operation, which includes the balance screening, takes place in approximately 60 seconds. The taking and storing of, in sequence and in any particular or desired order, the patient's age, sex, height, weight, BMI, and balance forces, thus characterize the screening operation. It is to be understood that if the patient's stability/balance score falls outside of the age-based balance/stability parameters, the patient is identified as a balance patient, requiring further assessment, diagnosis, and, perhaps, treatment.

In sum, system 90 functions to identify "balance patients," namely, patients with balance problems, and further functions to warn the doctor when a patient is at an increased risk of falling. System 90 allows a medical care professional to screen a patient and obtain a printed report with the patient's age, sex, height, weight, body mass index and stability/balance score, preferably in less than 60 seconds.

Once balance patients are identified in accordance with the invention, they then must be properly assessed. A focused, thorough medical history is the most important part of any such assessment. Also very important is a comprehensive physical evaluation that includes evaluating the patient's reflexes, sensation, muscle strength and tone, coordination, gait and stance. Since balance disorders are often vestibular in origin, they are frequently associated with hearing loss, thus audiometric testing is also essential. With the results of these first evaluations the physician can decide if more specifically focused tests (Table 1) are needed to select the appropriate clinical pathway for that patient.

TABLE 1

| Diagnostic Test | Importance level |
| --- | --- |
| Intelligent medical history | 5 |
| Physical examination | 5 |
| Audiometric testing | 4 |
| ENG/VNG | 4 |
| MRI | 3 |
| CT | 3 |
| Auditory brain stem response | 3 |
| Blood work | 3 |
| Rotary chair | 3 |
| Electrocochleography | 3 |
| EEG | 2 |
| Transcranial Doppler | 2 |
| Holter monitoring | 2 |
| Dynamic Posturography | 1 |
| Active head rotation testing | 1 |

Relative importance of diagnostic tests for a patient complaining of dizziness and balance disorders related symptoms (Blakley and Siegel, 1997):
5 = Extremely important for all patients;
4 = Very important and useful in most patients;
3 = important, and if done for the proper reasons, the result may affect treatment;
2 = some importance, but advisable only if specific symptoms of a particular illness other than dizziness are present;
1 = unimportant and probably unnecessary.

There are two basic underlying premises to this new proactive model, namely, 1)every patient's balance ability should be routinely and regularly checked as part of the normal patient examination, even if the patient doesn't complain of any symptoms related to balance; and 2)audiologists and physical therapists, providers who have the expertise required for the effective diagnosis and treatment of balance problems and who stand to benefit financially by being involved in the assessment of balance disorder patients, should be involved early-on in the collection of the information needed for an accurate diagnosis, relieving the primary care physician and his or her staff from the burden of performing those tasks but leaving the overall management of the patient's care in the hands of that physician. The essence of the second point is that the primary care physician, after having identified a patient with a balance impairment, would quickly determine if the condition had a clear and easily diagnosed origin, was a consequence of a known condition affecting that person (such as flu, lack of sleep, ingestion of OTC or prescription medications, etc.) or if the origins of the problem were unclear, unknown or uncertain. If the origins of the balance problem were unclear, unknown or uncertain, the physician would immediately refer the patient to an audiologist for an audiometric examination and to a physical therapist to do the physical evaluation. The audiologist or physical therapist would also collect a detailed, focused history from the patient.

The patient would then go back to the primary care physician with the compiled history and the results of the audiometric and physical evaluations. At that "problem-focused visit" the physician's staff would test the patient's intermediate vision. The physician would then decide if more exams were medically necessary, if the patient should be referred to a specialist, if the patient should be referred for therapy at that time, etc. The physician could bill for that visit.

If more specific tests were needed, they would most likely include an electronystagmography(ENG) and/or videonystagmography (VNG). When the ENG and/or VNG results were available, the patient would return to the primary care physician, who would then decide how to proceed, and who could then bill for another problem-focused visit. Because at some point almost all balance patients require balance and gait therapy, the physical therapist could also position himself as the provider of choice for those services. The balance center model, in accordance with the teachings of the invention, also provides for the involvement of an occupational therapist, as indicated, and after treatment, for the patient to participate in regular conditioning exercises such as tai chi.

In accordance with the invention, the primary care physician retains the control and management of his or her patient's care, effectively addressing his or her professional responsibility to that patient, but without significantly increasing the workload of the physician or his or her staff, and without increasing the cost of patient care paid by Medicare and other insurers, although the physician is adequately compensated for managing the patient's care. The audiologist is paid for the audiometric tests ordered by the physician, and sees many more new patients each month-patients referred by their physician. And since many balance patients have a hearing loss, the audiologist can also address that problem, selling hearing aids as needed. The audiologist might also be the provider of choice for any ENG/VNG tests ordered. The physical therapist also sees many more new patients each month, and is paid for both the physical evaluations and the therapy treatments.

In an average primary care setting, where the physician is seeing, for instance, 30 patients per day, with an average adult patient age of 52.5 years, it is estimated that an average of 60+ balance patients would be identified and referred to an audiologist and a physical therapist, each month, under the balance center model of the invention, resulting in some 120+ additional patient visits per month for the physician, with commensurate compensation for everyone involved in the patients' care. More importantly, it is those 60+ patients whose balance problems will have been identified, diagnosed and treated, whose quality of life will have been enhanced and for whom a number of devastating falls may have been prevented.

In sum, it is preferred that system 90 will measure patient weight, calculate patient BMI and provide patient stability/balance score, in which patient name, age, sex and height are obtained and entered manually, and that this process take place in approximately 60 seconds in accordance with the operation of system 90 as governed by software architecture 103. With the use of system 90, the balance center model of the invention functions to manage dizzy, balance disorder and falls risk patients, in which its underlying premise is that there are four steps to the effective management of such patients, namely, identification, assessment, diagnosis, and treatment.

§III. Conclusion

The present invention is described above with reference to preferred embodiments. Those skilled in the art will recognize that changes and modifications may be made in the described embodiments without departing from the nature and scope of the present invention. For instance, although the screening processes set forth herein are each preferably prosecuted in approximately 60 seconds, the objects and advantages of the invention are accomplished if the screening processes are each prosecuted at least within approximately five (5) minutes. Various changes and modifications to the embodiments herein chosen for purposes of illustration will readily occur to those skilled in the art. To the extent that such modifications and variations do not depart from the spirit of the invention, they are intended to be included within the scope thereof.

Having fully described the invention in such clear and concise terms as to enable those skilled in the art to understand and practice the same, the invention claimed is:

1. A method of screening a person for a balance disorder, comprising:
   entering a person's age and height into a computer;
   measuring force components and moments along one or more axes and one or more associated orthogonal axes exerted by the person while the person is standing on a force measuring apparatus; and
   comparing the measured force components and moments with age-based normative data to obtain a balance score for the person and to identify if the person has a balance problem or impairment,
   wherein said screening occurs in approximately 60 seconds or less.

2. A method according to claim 1, further comprising measuring the weight of the person with the force measuring apparatus.

3. A method according to claim 1, further comprising calculating the body-mass index of the person.

4. A method according to claim 1, further comprising conducting visual acuity testing of the person.

5. A method according to claim 1, further comprising conducting hearing acuity testing of the person.

6. A method according to claim 1, wherein the force measuring apparatus includes perturbing foam.

7. A method according to claim 1, wherein said screening is performed by a primary care physician as part of a routine evaluation, even if the person does not complain of symptoms related to balance.

8. A method according to claim 7, further comprising identifying whether the person has a balance impairment as a consequence of a known condition affecting the person.

9. A method according to claim 7, further comprising referring the person to an audiologist for audiometric testing.

10. A method according to claim 7, further comprising referring the person to a physical therapist for physical evaluation.

11. A method according to claim 10, wherein the physical evaluation includes evaluating the person's reflexes, sensation, muscle strength and tone, coordination, gait, and stance.

12. A method according to claim 7, further comprising audiometric and physical evaluation of the person by ancillary medical personnel, alter which the person returns to the primary care physician to determine if additional medical tests are necessary.

13. A method according to claim 12, further comprising conducting at least one test selected from the group consisting of electronystagmography, videonystagmography, MRI, CT, rotary chair, and electrocochleography.

14. A method according to claim 1, wherein the force measuring apparatus comprises a force platform.

15. A method according to claim 14, wherein the force platform is substantially flat.

16. A method according to claim 1, wherein the measuring of force components and moments occurs while the person is in various forms of stance.

17. A method according to claim 12, further comprising conducting at least one test selected from the group consisting of electronystagmography, videonystagmography and electrocochleography.

18. A method of screening and assessing a patient for a balance disorder, comprising:
   inputting patient specific information into a computer;
   measuring force components and moments along one or more axes and one or more associated orthogonal axes exerted by the patient while the patient is standing on a substantially flat force platform arrangement;
   calculating a balance score for the patient; and
   comparing the measured force components and moments with age-based normative parameters to identify if the patient has a balance problem;
   wherein the screening occurs in less than about 60 seconds.

* * * * *